United States Patent
Ma et al.

(10) Patent No.: US 11,369,278 B2
(45) Date of Patent: Jun. 28, 2022

(54) METHODS AND SYSTEMS FOR DETERMINING LUMEN VOLUME AND CORONARY BLOOD FLOW

(71) Applicant: Keya Medical Technology Co., Ltd., Beijing (CN)

(72) Inventors: Bin Ma, Bellevue, WA (US); Shubao Liu, College Park, MD (US); Xiaoxiao Liu, Bellevue, WA (US); Bin Ouyang, Shenzhen (CN); Qi Song, Seattle, WA (US)

(73) Assignee: BEIJING KEYA MEDICAL TECHNOLOGY CO., LTD., Beijing (CN)

( * ) Notice: Subject to any disclaimer, the term of this patent is extended or adjusted under 35 U.S.C. 154(b) by 518 days.

(21) Appl. No.: 16/178,574

(22) Filed: Nov. 1, 2018

(65) Prior Publication Data
US 2019/0159683 A1    May 30, 2019

Related U.S. Application Data

(60) Provisional application No. 62/591,437, filed on Nov. 28, 2017.

(51) Int. Cl.
*G16H 30/40* (2018.01)
*A61B 6/00* (2006.01)
(Continued)

(52) U.S. Cl.
CPC ............ *A61B 5/026* (2013.01); *A61B 5/1073* (2013.01); *A61B 6/481* (2013.01); *A61B 6/486* (2013.01);
(Continued)

(58) Field of Classification Search
CPC ................................ A61B 6/504; A61B 6/481
See application file for complete search history.

(56) References Cited

U.S. PATENT DOCUMENTS

| | | | |
|---|---|---|---|
| 2012/0229504 A1* | 9/2012 | Nakamura | A61B 6/469 345/629 |
| 2014/0088414 A1 | 3/2014 | Mittal et al. | |

(Continued)

FOREIGN PATENT DOCUMENTS

| | | |
|---|---|---|
| CN | 102258381 A | 11/2011 |
| CN | 104463844 A | 3/2015 |
| CN | 106667513 A | 5/2017 |

OTHER PUBLICATIONS

Wong, J. T., Kamyar, F., & Molloi, S. (2007). Quantitative coronary angiography using image recovery techniques for background estimation in unsubtracted images. Medical physics, 34(10), 4003-4015. (Year: 2007).*

(Continued)

*Primary Examiner* — Carolyn A Pehlke
*Assistant Examiner* — Johnathan Maynard
(74) *Attorney, Agent, or Firm* — Bayes PLLC

(57) ABSTRACT

The disclosure provides a method and system for determining a lumen volume of a target blood vessel. The method may include acquiring a temporal sequence of angiography images of the target blood vessel after a contract agent is injected in the target blood vessel. The method may further include identifying a region of interest containing the target blood vessel, by a processor, in each angiography image in the temporal sequence of angiography images. The method may also include integrating, by the processor, pixel values in each region of interest, and determining the lumen volume, by the processor, based on the integrated values of the (Continued)

regions of interest and a predetermined correlation between the integrated values and volumes of the contrast agent.

21 Claims, 10 Drawing Sheets

(51) Int. Cl.
  *A61B 5/00* (2006.01)
  *A61B 5/026* (2006.01)
  *A61B 5/107* (2006.01)
  *G06T 7/00* (2017.01)
(52) U.S. Cl.
  CPC ............ *A61B 6/504* (2013.01); *A61B 6/5217* (2013.01); *A61B 6/5235* (2013.01); *G16H 30/40* (2018.01); *A61B 5/489* (2013.01); *A61B 6/469* (2013.01); *G06T 7/0016* (2013.01); *G06T 2207/30104* (2013.01)

(56) References Cited

U.S. PATENT DOCUMENTS

| | | | |
|---|---|---|---|
| 2016/0089100 A1* | 3/2016 | Korporaal | A61B 6/541 600/431 |
| 2017/0007195 A1 | 1/2017 | Molloi | |

OTHER PUBLICATIONS

Fallavollita, P., & Cheriet, F. (Aug. 2007). Robust coronary artery tracking from fluoroscopic image sequences. In International Conference Image Analysis and Recognition (pp. 889-898). Springer, Berlin, Heidelberg. (Year: 2007).*

Hubbard, L., Ziemer, B., Lipinski, J., Sadeghi, B., Javan, H., Groves, E. M., . . . & Molloi, S. (2016). Functional assessment of coronary artery disease using whole-heart dynamic computed tomographic perfusion. Circulation: Cardiovascular Imaging, 9(12), e005325. (Year: 2016).*

Wong, J. T., Ducote, J. L., Xu, T., Hassanein, M. T., & Molloi, S. (2006). Automated technique for angiographic determination of coronary blood flow and lumen volume. Academic radiology, 13(2), 186-194. (Year: 2006).*

Molloi, S., Kassab, G. S., & Zhou, Y. (2001). Quantification of coronary artery lumen volume by digital angiography: in vivo validation. Circulation, 104(19), 2351-2357. (Year: 2001).*

Molloi, S., Bednarz, G., Tang, J., Zhou, Y., & Mathur, T. (1998). Absolute volumetric coronary blood flow measurement with digital subtraction angiography. The International Journal of Cardiac Imaging, 14(3), 137-145. (Year: 1998).*

Molloi, S. et al., "Absolute volumetric coronary blood flow measurement with digital substraction angiography", International Journal of Cardiac Imaging (1998) 14: pp. 137-145, https://doi.org/10.1023/A:1006059709539, 9 pages.

Wong, Jerry T. et al., "Automated Technique for Angiographic Determination of Coronary Blood Flow and Lumen Volume", Acad Radiol. Feb. 2006;13(2): pp. 186-194, 9 pages.

Zhang, Zhang et al., "Quantification of absolute coronary flow reserve and relative fractional flow reserve in a swine animal model using angiographic image data", American Journal of Physiology—Heart and Circulatory Physiology 303.3 (2012): H401-H410, 10 pages.

Telea, Alexandru, "An Image Inpainting Technique Based on the Fast Marching Method", Journal of Graphics, GPU, and Game Tools, vol. 9, No. 1, pp. 25-36 (2004), 12 pages.

Farnebäck, Gunnar, "Two-Frame Motion Estimation Based on Polynomial Expansion", Proceedings of the 13th Scandinavian Conference on Image Analysis. Gothenburg, Sweden, 2003, 8 pages.

Kitamura, K. et al., "Estimating the 3D Skeletons and Transverse Areas of Coronary Arteries from Biplane Angiograms", IEEE Transactions on Medical Imaging, Vo.7, No. 3 (1988): pp. 173-187.

Office Action in corresponding Chinese Application No. 201811426619.3 dated Oct. 11, 2021 (11 pages).

* cited by examiner

700 acquire a sequence of angiography images of the target blood vessel injected with contrast agent ～ 702

Identify a corresponding ROI containing the target blood vessel in each angiography image ～ 704

Integrate the background removed and logarithmically processed intensity values of the pixels for the ROI ～ 706

Determine a flow rate of the target blood vessel ～ 708

FIG. 7

METHODS AND SYSTEMS FOR DETERMINING LUMEN VOLUME AND CORONARY BLOOD FLOW

CROSS REFERENCE TO RELATED APPLICATION

This application claims the benefit of priority to U.S. Provisional Application No. 62/591,437, filed on Nov. 28, 2017, the entire content of which is incorporated herein by reference.

TECHNICAL FIELD

The present disclosure generally relates to image processing and analysis. More specifically, the present disclosure relates to a computer-implemented method and system for determining a lumen volume and a coronary blood flow of a target blood vessel.

BACKGROUND

Blood circulation is one of the most important functions in the body, which supplies oxygen to the body's organs. For example, coronary circulation is the circulation of blood within the blood vessels of the heart muscle (also known as myocardium). The coronary artery delivers oxygen-rich blood to the myocardium. A severe coronary artery stenosis can limit myocardial blood flow, resulting in myocardial ischemia. However, the ability of a cardiologist to distinguish lesions that can cause myocardium ischemia from lesions that are physiologically insignificant based on coronary angiography alone is limited. Volumetric coronary blood flow assessed as a function of time may be a valuable aid in the analysis of functional significance of arterial obstruction. For instance, when assessing the physiological significance of an epicardial stenosis using fractional flow reserve (FFR), blood flow may be used as one or more boundary conditions to calculate quantitative FFR. Diagnosis and understanding of microvascular disease may use absolute blood flow for better understanding of many pathophysiological conditions such as heart transplantation, stem cell therapy, and large transmural myocardial infarction.

Existing angiographic methods to assess coronary arterial blood flow are based on analysis of the propagation of contrast agent following an injection of contrast agent through the circulatory system. The flow information is then determined using the contrast agent pass curve data measured in the epicardial arteries or the myocardial perfusion bed. Accordingly, absolute mean and instantaneous coronary blood flow can be determined from a first-pass analysis (FPA). These techniques determine coronary blood flow by quantifying the amount of contrast agent that fills a selected region of interest (ROI) and measuring the change in videodensitometric signal in successive images. In addition, a digital angiography technique has been developed to quantify coronary arterial lumen volume with high accuracy. This technique uses a background subtracted image and a carefully drawn ROI around coronary arteries to quantify lumen volume from the integrated videodensitometric signal inside the ROI and a system calibration factor. These techniques often make assumptions that contrast agent concentration and x-ray beam energy are known and either match the calibration conditions or are interpolated from the calibration table. An external calibration, together with additional corrections on magnification, is generally required to perform the method. Also, the ROI area is usually manually chosen. Background subtraction usually relies on phase-match guided by external ECG signal.

According to the FPA approach in the traditional methods, the volume of the vascular bed, which is supplied by a major coronary artery, is modeled as a reservoir with a single input. Coronary blood flow may be determined from the change in volume during one cardiac cycle as shown in FIG. 1.

The first-pass analysis simplifies the coronary arterial system as a collection volume (Vp) receiving a single input at a flow rate of Q and no knowledge of the arterial structures in the system or routes of exit is required. Additionally, there is a brief period when the entering contrast agent collects inside Vp without any of it leaving. Then, before any contrast agent leaves the selected perfusion volume, Q may be determined from the change in contrast volume (V) over the change in time (t): $Q = \Delta V / \Delta t$. Application of the first-pass analysis generally involves identifying a proximal arterial segment in which coronary blood flow will be measured and its distal network of vessels in which the injected contrast agent will collect before emptying into the capillary and venous systems. Contrast agent propagation through the arterial network may then be monitored with the acquired images, such as a spatially varying videodensitometric iodine signal. For a known concentration of iodine (CI) in the contrast agent, videodensitometry may quantify the volume of contrast agent in the coronary arterial system based on the iodine signal. The concentration of the contrast agent is usually known by injecting contrast agent at a rate faster than the coronary blood flow so that the injected bolus of contrast agent completely replaces the blood. In such a case, the volume of the contrast agent (V) is equal to the detected iodine mass (MI) divided by its concentration: $V = MI/CI$. The total coronary arterial volume may then be determined from the volume of the contrast agent measured before the filling of the capillary and venous systems.

In one example, the average flow rate of the contrast agent for a time period $\Delta t$ may be written as Equation (1).

$$\bar{Q} = \frac{1}{C} \frac{A}{\left(\frac{\mu}{\rho}\right)_I} \frac{\Delta D_I}{\Delta t}, \qquad \text{Equation (1)}$$

wherein $\Delta D_I$ is the change in the integrated videodensitometric iodine signal over the ROI in the image. The mass attenuation coefficient of iodine $$\left(\frac{\mu}{\rho}\right)_I$$

and the pixel area A are measured using an iodine calibration phantom. The iodine concentration C (g/cm³) of the bolus entering the myocardial perfusion bed is assumed to be the same as the iodine concentration of the contrast agent. This flow measurement technique utilizes the integrated videodensitometric signal to determine the volume change of contrast agent within the perfusion volume of interest. The system iodine calibration slope and the known iodine concentration of the contrast agent are used to convert the integrated videodensitometric signal to the volume of the contrast agent. Variation in the iodine mass attenuation coefficient may be caused by changes in patient chest thickness, x-ray beam energy and residual scatter-glare fraction. To account for x-ray beam energy and x-ray setup geometric variations, the system iodine calibration is repeated for every imaging projection or is simplified by a two-dimensional lookup table based on the minimum tissue thickness ($T_{min}$) and x-ray beam energy (kVp). Additionally or alternatively, an image of a calibration phantom positioned over the heart is acquired to determine the correlation between the image gray level and the iodine mass. Additional corrections may be needed for changes of a higher magnitude.

However, these traditional methods relay on the assumption that the concentration of the actually injected contrast agent is the same as that used in the calibration process. In addition, the methods also require several external corrections that increase uncertainties.

Embodiments of the disclosure address the above problems by a computer-implemented method and device for determining a lumen volume and a coronary blood flow of a target blood vessel.

SUMMARY

A computer-implemented method, a system, and a non-transitory computer-readable storage medium for determining a lumen volume of a target blood vessel are disclosed. The disclosed method may calculate the lumen volume and/or the flow of the target blood vessel, without relying on the external calibrations such as the calibration phantom and two-dimensional lookup table. The fully automatic self-calibration decreases the uncertainties in the calculation process, and increases the accuracy of the calculation results.

In an aspect, the present disclosure relates to a computer-implemented method for determining a lumen volume of a target blood vessel. The method may include acquiring a temporal sequence of angiography images of the target blood vessel after a contrast agent is injected in the target blood vessel. The method may further include identifying a region of interest containing the target blood vessel, by a processor, in each angiography image in the temporal sequence of angiography images. The method may also include integrating, by the processor, pixel values in each region of interest, and determining the lumen volume, by the processor, based on the integrated values of the regions of interest and a predetermined correlation between the integrated values and volumes of the contrast agent.

In another aspect, the present disclosure relates to a system for determining a lumen volume of a target blood vessel. The system may include an interface and a processor. The interface may be configured to receive a temporal sequence of angiography images of the target blood vessel acquired after a contrast agent is injected in the target blood vessel. The processor may be configured to identify a region of interest containing the target blood vessel in each angiography image in the temporal sequence of angiography images. The processor may also be configured to integrate pixel values in each region of interest. The processor is further configured to determine the lumen volume based on the integrated values of the regions of interest and a predetermined correlation between the integrated values and volumes of the contrast agent.

In yet another aspect, the present disclosure is directed to a non-transitory computer-readable storage medium having computer executable codes stored thereon. The computer executable codes, when executed by a processor, perform a method for determining a lumen volume of a target blood vessel. The method may include receiving a temporal sequence of angiography images of the target blood vessel acquired after a contrast agent is injected in the target blood vessel. The method may further include identifying a region of interest containing the target blood vessel, by a processor, in each angiography image in the temporal sequence of angiography images. The method may also include integrating, by the processor, pixel values in each region of interest, and determining the lumen volume, by the processor, based on the integrated values of the regions of interest and a predetermined correlation between the integrated values and volumes of the contrast agent.

BRIEF DESCRIPTION OF THE DRAWINGS

In the drawings, which are not necessarily drawn to scale, like numerals may describe similar components in different views. The drawings illustrate generally, by way of example, but not by way of limitation, various embodiments, and together with the description and claims, serve to explain the disclosed embodiments. When appropriate, the same reference numbers are used throughout the drawings to refer to the same or like parts. Such embodiments are demonstrative and not intended to be exhaustive or exclusive embodiments of the present method, device, system, or non-transitory computer readable storage medium having instructions stored thereon for implementing the method.

FIG. 7 is a flowchart of an exemplary process of the method for determining an average flow rate of a target blood vessel according to an embodiment of the present disclosure;

DETAILED DESCRIPTION

Figure 1:
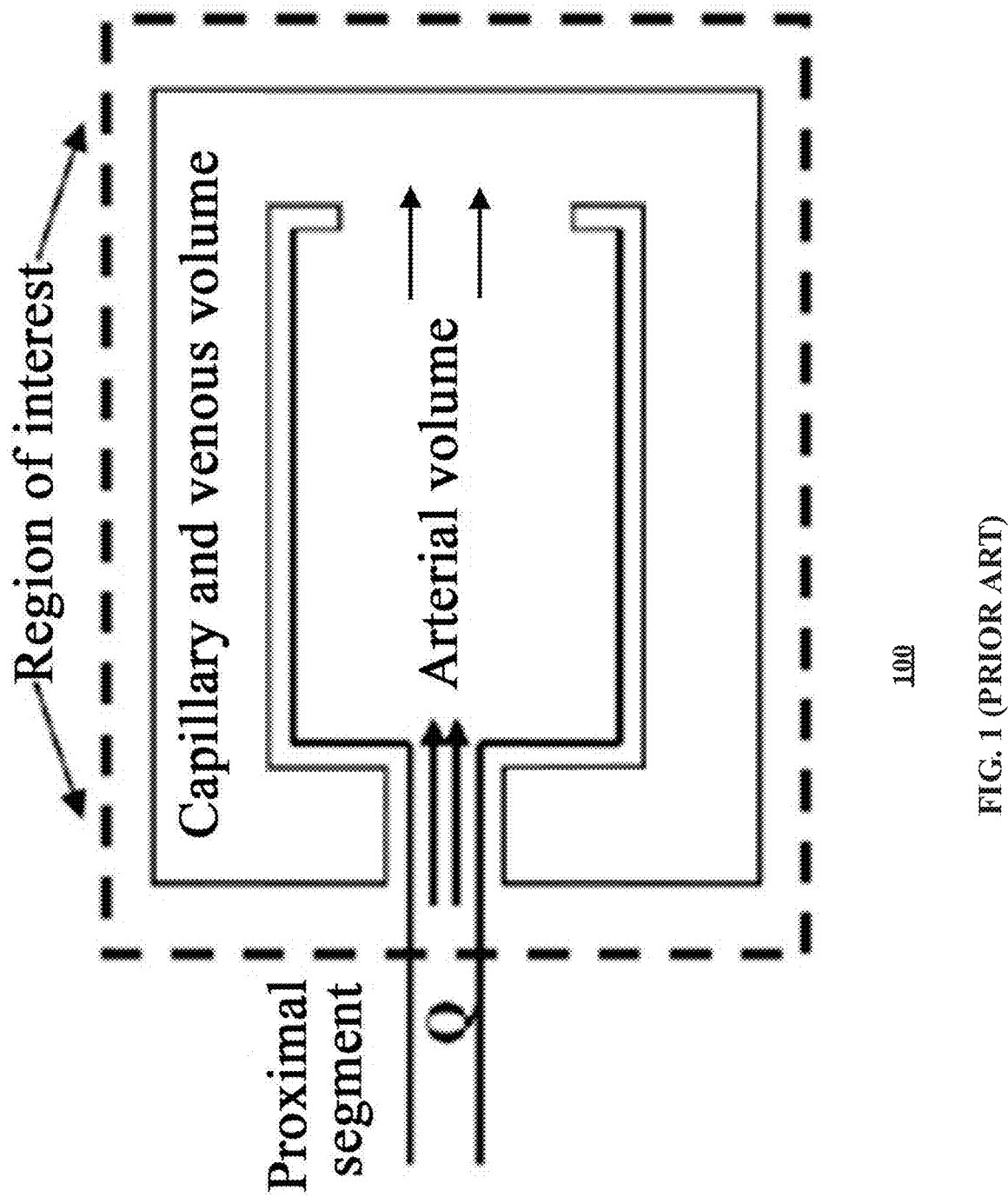
FIG. 1 illustrates a simplified model of the first-pass analysis.

Various aspects and features of the present disclosure are described herein with reference to the drawings. These and other features of the present invention will become apparent from the following description of the preferred form of the embodiments given as a non-limiting example with reference to the accompanying drawings.

This specification may use the phrases "in one embodiment," "in another embodiment," "in yet another embodiment," or "in other embodiments," to refer to one or more of the same or different embodiments in the present disclosure. Note that, throughout the specification, the same reference numerals denote the same or similar elements, and unnecessary redundant descriptions are omitted. Moreover, an element which appears in a singular form in the specific embodiments do not exclude that it may appear in a plurality (multiple) form.

The technical term "optical path" used herein refers to the geometric path of rays propagating within a subject (not a vacuum). The technical term "optical path length" refers to the length of a geometric path along which the rays propagate in the subject. The term "simulated optical path length" refers to the length of the optical path obtained by simulation based on a model. An "image of a blood vessel" refers to an image that shows, among other things, a blood vessel. The technical term "flow of the blood vessel" used herein may refer to the flow rate of the fluid within the lumen of the blood vessel, such as the diffusing flow rate of the injected contrast agent therein. When the injection operation of the contrast agent is completed, its diffusion flow rate in the blood vessel may approximate the flow rate of the blood in the blood vessel.

Figure 2:
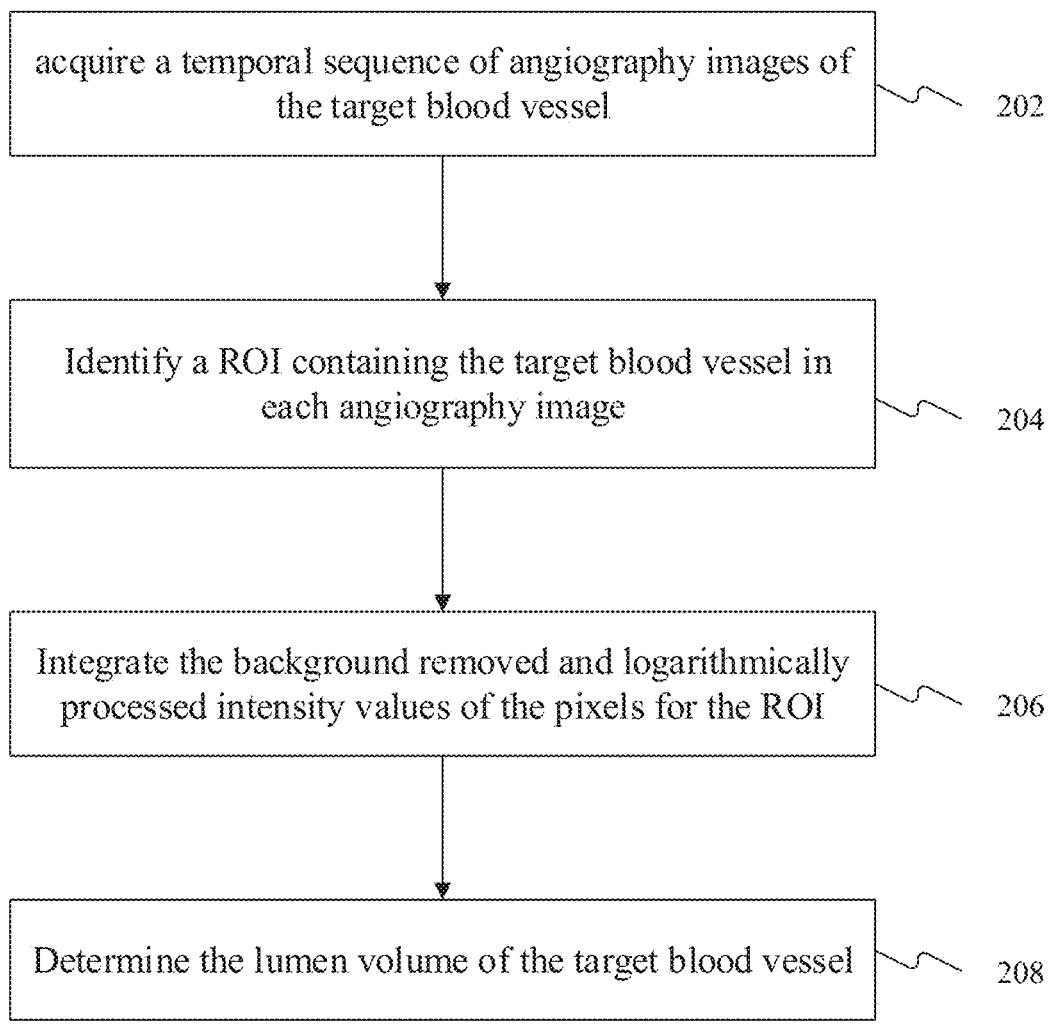
FIG. 2 shows a flowchart of an exemplary process for determining a lumen volume of a target blood vessel according to an embodiment of the present disclosure.

FIG. 2 shows a flowchart of an exemplary process 200 for determining a lumen volume of a target blood vessel according to an embodiment of the present disclosure. The process 200 begins with step 202 to acquire a temporal sequence of angiography images of the target blood vessel. In some embodiments, the target blood vessel may be a diseased blood vessel selected by the user or determined by a machine. In an example, the temporal sequence of angiography images of the target blood vessel may be obtained by injecting the contrast agent into the target blood vessel and performing continuous imaging of the target blood vessel by means of an imaging device. In some embodiments, the angiography images in the sequence may be acquired in a time order. However, the sequence does not necessarily include each frame acquired, but only selected image frames.

Figure 3:
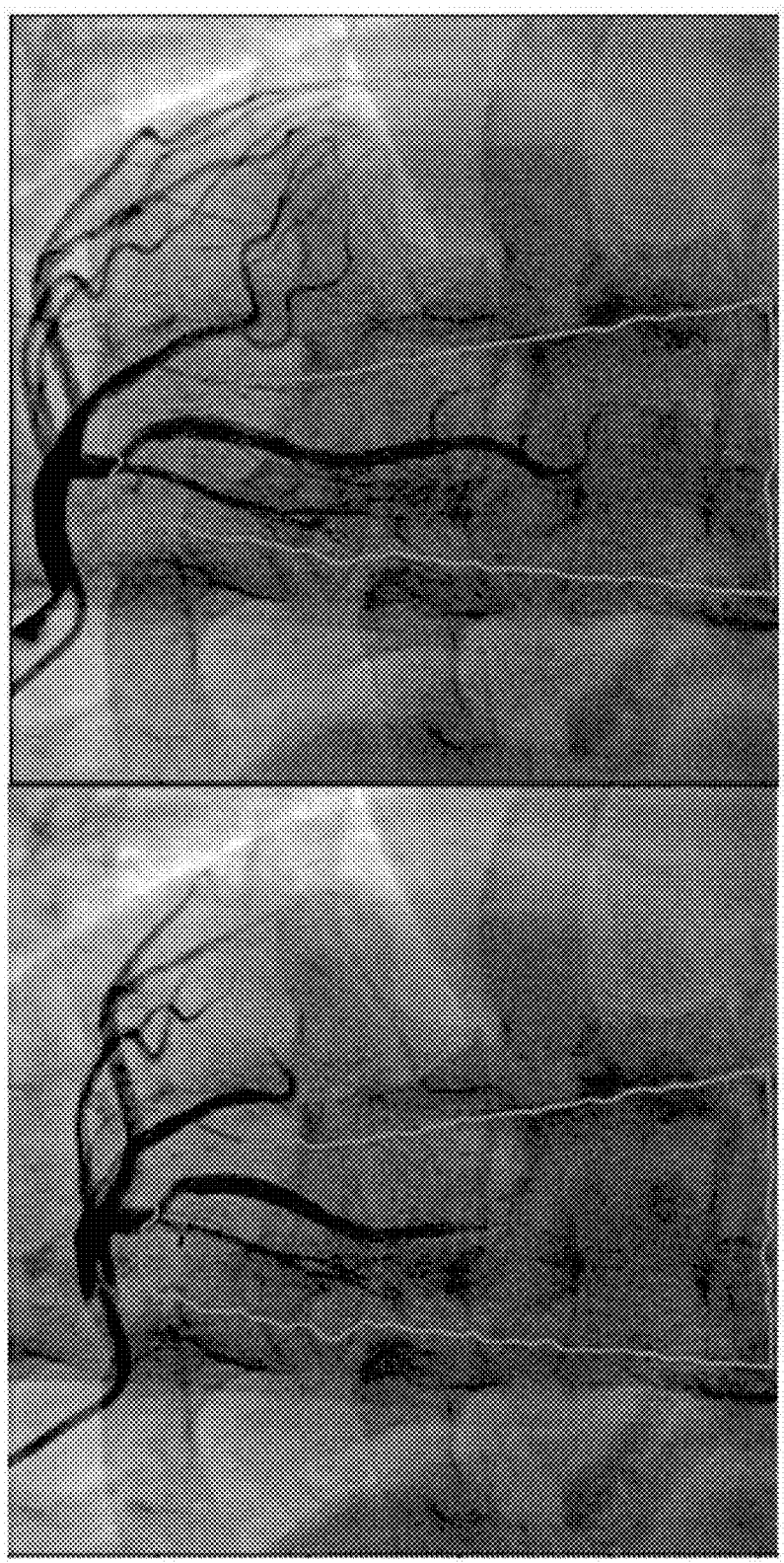
FIG. 3 shows an example of the angiography image sequence and an ROI tracked across the sequence according to an embodiment of present disclosure.

An exemplary sequence of angiography images is shown in FIG. 3. The contrast agent gradually diffuses into the blood vessel between image (a) and image (b). Although only two angiography images as shown in FIG. 3, it is contemplated that the sequence of the angiography images may include more (e.g. three or more) angiography images of the target blood vessel.

In step 204, a ROI containing the target blood vessel is identified in each image in the sequence. In some embodiments, each ROI including the target blood vessel may be obtained along the centerline of the blood vessel of the corresponding angiography image. In some embodiments, the ROI including the target blood vessel may be obtained by tracking the target blood vessel across the plurality of angiography images using an optical flow algorithm. In an example, a Farneback optical flow algorithm may be used, which provides a good tradeoff between tracking accuracy and speed. FIG. 3 illustrates the tracking of the ROIs. In the sequence of angiography images, vessels and other tissues move from frame to frame. In some embodiments, the corresponding ROI may be tracked using the optical flow algorithm, in order to accurately compute the volume of the contrast agent of the corresponding ROI across different frames. In one embodiment, the envelope boundary of the ROI may be tracked by the optical flow, which is highlighted as shown in FIG. 3. Relying on the relative high contrast of the vessel, a tracked envelope boundary is determined to keep the vessel of interest in the ROI.

In step 206, an integrated value calculation may be performed for each angiography image by processing the intensity values of the pixels within the ROI of the angiography image and integrating the processed pixel values. In some embodiments, the processing may include removing background pixels and logarithmically processing the pixel values. In some embodiments, the integrated value may be calculated by summing the intensity values of the pixels in the ROI of the processed image. Consistent with the disclosure, the integrated value may be referred to as "integrated signal."

Figure 4:
FIG. 4 illustrates angiography images processed according to an embodiment of the present disclosure.

FIG. 4 illustrates angiography images processed according to an embodiment of the present disclosure. Image (a) is a two-dimensional image of the target blood vessel $I_T$ (e.g. the angiography image). The ROI may be only a part of the whole region as shown in image (a), which may only contain a section or a portion of the blood vessel therein. In some embodiments, the ROI may be set by the user (such as the physician) as needed.

Image (b) is a background image $I_B$ of the two-dimensional image $I_T$, which is what the two-dimensional image $I_T$ should look like without an injected contrast agent. In some embodiments of the present disclosure, the background image may be estimated using image inpainting methods. For example, the blood vessels may be segment and extracted from the image, and then the vessel area may be replaced based on information from its surrounding area. In some embodiments, various image inpainting methods may be adopted focusing on different aspects of structures in the image, including geometric structure, texture, etc. In one embodiment, an image inpainting method may be selected, which matches the gradient vector at the boundary of the inpainting region and has a good balance between accuracy and speed. For example, image (b) illustrates an image inpainting method by filling in the vessel region by matching the background intensity patterns (such as the bright artifact region). In some extended embodiments, the above inpainting may be done in video sequence in order to better preserve the temporal consistency.

Although image inpainting is described in the present disclosure as an exemplary method to estimate the background image and remove the same, it is contemplated that any other known background image estimation method may be used to estimate the background image.

In some embodiments, the first processed image $\ln(I_T)-\ln(I_B)$ may be obtained by the following steps. Firstly, the logarithm of an intensity value of each pixel for the two-dimensional image $I_T$ (as shown in FIG. 4(a)) may be calculated, to obtain a second logarithmically processed image $\ln(I_T)$. Then, the vessel portion therein may be inpainted based on the intensity values of the background pixels within its surrounding region, to obtain the estimated background image $I_B$ (e.g. image (b)). After that, the logarithm of the intensity value of each pixel for the estimated background image $I_B$ may be calculated, to obtain a third logarithmically processed image $\ln(I_B)$. The third logarithmically processed image $\ln(I_B)$ may be subtracted from the second logarithmically processed image $\ln(I_T)$, to obtain the first processed image $\ln(I_T)-\ln(I_B)$ (e.g., image (c)). Then, the intensity values of all the pixels in the ROI of the first processed image $\ln(I_T)-\ln(I_B)$ may be summed to obtain the above described integrated value.

Returning to FIG. 2, process 200 may proceed to step 208 to determine the blood vessel lumen volume. In some embodiments, the lumen volume of the target blood vessel may be determined based on the integrated values calculated by step 206 for the plurality of angiography images and a predetermined correlation between the integrated value and volume of the contrast agent.

Figure 5:
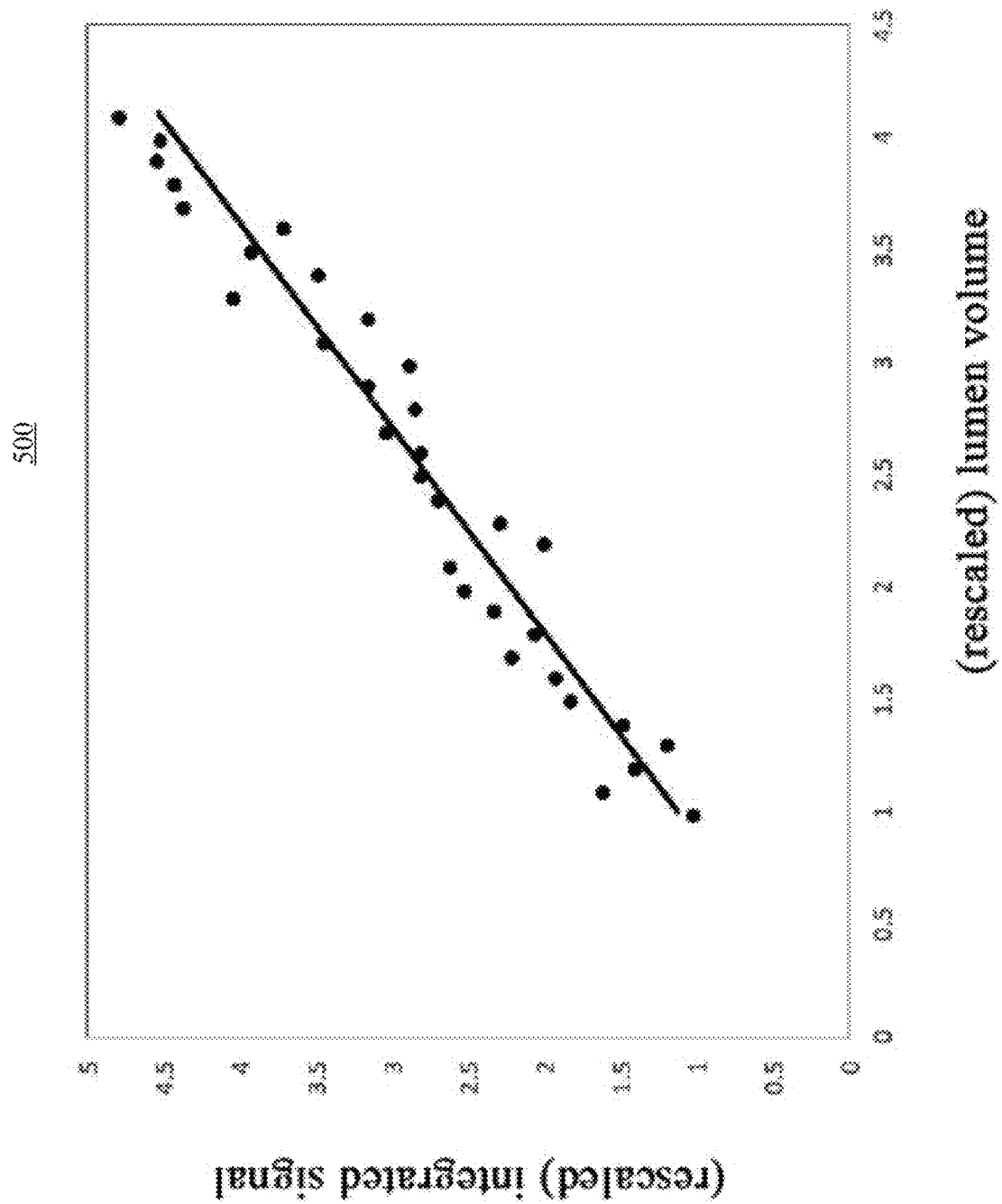
FIG. 5 is a diagram illustrating a correlation between an integrated signal and a volume of the contrast agent according to an embodiment of the present disclosure.

A predetermined correlation exists between the integrated value calculated for the ROI including the target blood vessel and the volume of the contrast agent injected into the target blood vessel. As shown in FIG. 5, the respect points are plotted with the volume of the contrast agent as the lateral axis and the integrated signal as the vertical axis. It can be seen from FIG. 5 that the predetermined correlation between the integrated signal (i.e., the integrated value) and the volume of the contrast agent may be fitted as a linear correlation. Therefore, the predetermined correlation between the integrated signal (i.e., the integrated value) and the volume of the contrast agent may be determined in advance. In this manner, by means of the correlation determined in advance and the integrated value calculated for the ROI (where the target blood vessel locates) of the current angiography image, the volume of the contrast agent in the ROI of the current angiography image may be calculated on the fly. The volumes of the contrast agent filled in the target blood vessel in the angiography images acquired at different timing may be calculated.

In some embodiments, step 208 may be implemented by calculating the volumes of the contrast agent in the corresponding ROIs in the plurality of angiography images based on the integrated values calculated by step 206 for the plurality of angiography images and the predetermined correlation, and determining the largest one among the calculated volumes of the contrast agent as the lumen volume of the target blood vessel.

In some other embodiments, step 208 may be implemented by selecting the largest integrated value among the integrated values calculated for the plurality of angiography images, and calculating the volume of the contrast agent corresponding to the largest integrated value as the lumen volume of the target blood vessel based on the largest integrated value and the predetermined correlation (e.g. the linear correlation as shown in FIG. 5).

It is observed that the volume of the contrast agent increases gradually for a certain period from injecting the contrast agent, during which the contrast agent flows into the target blood vessel and does not flow out of the target blood vessel, until reaching its largest volume. Then, as time goes on, the contrast agent flows gradually out of the target blood vessel, and thus the volume of the contrast agent will decrease gradually. Therefore, the largest value of the volume of the contrast agent may be used to approximate the lumen volume of the target blood vessel.

The above-mentioned predetermined correlation (e.g., a linear correlation) f is also supported mathematically. Specifically, the correlation between x-ray attenuation and optical path in the contrast agent may be defined by following Equation (2).

$$\frac{I_T}{I_I} = \exp[-(\mu_C/\rho_C)x_C - (\mu_o/\rho_o)x_o] \quad \text{Equation (2)}$$

where $I_I$ is the incident beam intensity, $I_T$ is the transmitted beam intensity, $\Delta\mu/\rho$ is the mass attenuation coefficient and x is the optical path. The technical term "optical path" herein refers to the geometric path of x-rays propagating within a subject (not a vacuum). In addition, the subscripts c and o represent "contrast agent" and "organ" (i.e. vessel), respectively. In the absence of a contrast agent, the x-ray beam absorption, due to the organ alone, is described by Equation (3).

$$\frac{I_B}{I_I} = \exp[-(\mu_o/\rho_o)x_o] \quad \text{Equation (3)}$$

where $I_B$ is the transmitted beam intensity with only background.

By substituting Equation (3) into Equation (2), the correlation between the intensity of the light transmitted through the blood vessel at each position and the optical path length $x_c$ at the corresponding positions can be obtained, see Equation (4).

$$x_C = \frac{\rho_C}{\mu_C}[\ln(I_T) - \ln(I_B)] \quad \text{Equation (4)}$$

The light transmitted through the blood vessel at each position thereof may be incident onto a flat panel detector, which captures a gray-scale two-dimensional image. Thereby, the intensity of the light transmitted through the blood vessel at each position is converted to an intensity value (for example, a grayscale value) at the corresponding position of the blood vessel in the two-dimensional image. The conversion to gray-scale does not destroy the described predetermined (inherent) correlation. Accordingly, the inherent correlation between the intensity of the light transmitted through the blood vessel at each position and the optical path length $x_c$ at the corresponding position is maintained between the intensity value at each position of the blood vessel in the two-dimensional image and the optical path length $x_c$ at the corresponding position. Hereinafter, for the purpose of description, the conversion between the intensity of the light transmitted through the blood vessel at each position and the intensity value at each corresponding position of the blood vessel in the two-dimensional image is ignored, and $I_T$ is used to denote the intensity value at each position of the blood vessel in the two-dimensional image, and $I_B$ is used to denote the background intensity value at the corresponding position of the blood vessel in the two-dimensional image.

Further, the contrast agent sample volume $V_0$ may be considered a cuboid whose volume is the multiple of a pixel area A and an optical path $x_c$, as shown by Equation (5).

$$V_0 = Ax_C = -A\left(\frac{\rho_C}{\mu_C}\right)[\ln(I_T) - \ln(I_B)] \quad \text{Equation (5)}$$

It can be seen that the contrast agent sample volume $V_0$ has a linear correlation with the processed intensity value $[\ln(I_T) - \ln(I_B)]$ of the sampling point, which is resulted by removing background and logarithmically processing therefor. Integration operation for the ROI where the target blood vessel locates may be performed for both sides of the equality sign in Equation (5), and such linear correlation still maintains between the lumen volume of the blood vessel (corresponding to the volume of the contrast agent) V and the integrated value of $[\ln(I_T) - \ln(I_B)]$.

In some embodiments, the predetermined correlation may be established in advance in previous angiography of the same patient under the same contrast agent injection condition. In some embodiments, the predetermined correlation may be established in advance for part of the blood vessel in the same angiography. This is because difference in physiological characteristics (such as blood viscosity, respiratory motion, cardiac motion, etc.) and/or contrast agent parameters (such as injection time and injection volume) may be small for the same patient. Therefore, the correlation established in advance in the previous angiography or for part of the blood vessel in the same angiography can be continuously adapted to the same patient. As a result, it may obtain the predetermined correlation between the integrated value and the volume of the contrast agent quickly, and thus may determine the lumen volume of the target blood vessel on the fly for the same patient.

Figure 6:
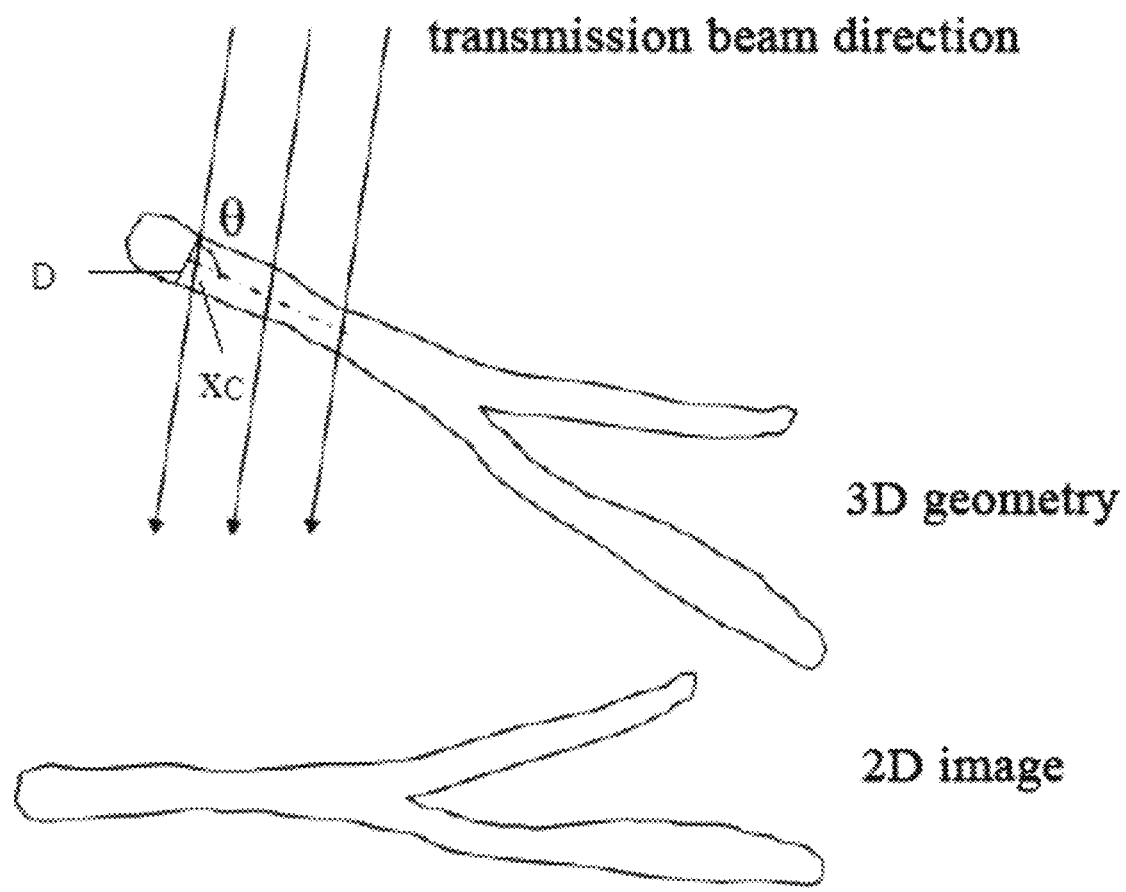
FIG. 6 is a schematic illustration of an optical path calculation process according to an embodiment of the present disclosure.

The above described predetermined correlation may be obtained, e.g. by the following process. The actual optical path $x_c$ at a pixel may be obtained through radius estimation based on the original X-ray angiograph images (optionally accounting for 3D-2D projection relation), as described by Equation (6) and in connection with FIG. 6.

$$x_c = D/\sin\theta \qquad \text{Equation (6)}$$

where D is the vessel diameter at the corresponding pixel and $\theta$ is the angle between the vessel centerline at the corresponding pixel and the x-ray projection direction. The vessel diameter D and the angle $\theta$ may be obtained through image analysis, to calculate the optical path at a sample point (which may be set e.g. along the centerline of the target blood vessel).

As an example, if the background removed and logarithmically processed intensity value $\ln(I_T)-\ln(I_B)$ of the individual sample point is considered as the integrated signal at the corresponding sample point, the integrated signal at the sample point may be plotted against the contrast agent sample volume $V_0$, as shown in FIG. 5. FIG. 5 establishes the correlation between the integrated signal (i.e., the integrated value) and the volume of the contrast agent V. Compared with traditional approaches, the method according to embodiments of present disclosure may obtain the correlation between integrated signal and lumen volume of the blood vessel based on the images and does not rely on external calibrations.

In some embodiments, the plurality of angiography images are selected from a sequence of angiography images acquired after a first predetermined time elapses from the starting time of injection. In one example, during a first predetermined time from injection of the contrast agent is started, e.g. 10 seconds after the injection of the contrast agent is started, the contrast agent has not flowed into the ROI. Accordingly, the volume of the contrast agent needs not to be calculated till the first predetermined time ends, and the processing speed is accelerated.

In some embodiments, the first predetermined time may be set to be relatively large. Theoretically, it may be set before when the contrast agent begins to flow out of the target blood vessel to satisfy the needs. Therefore, the first predetermined time may be set according to priori knowledge, and is not limited to the particular time described above.

An exemplary process 700 of the method for determining a flow rate of a target blood vessel is shown in FIG. 7. The exemplary process 700 begins with an acquiring step 702. In step 702, a temporal sequence of angiography images may be acquired for the target blood vessel injected with the contrast agent. In step 704, a corresponding ROI including the target blood vessel may be identified for each of the sequential plurality of angiography images in the sequence of the angiography images. In step 706, the background removed and logarithmically processed intensity values of the pixels may be integrated for the ROI. Steps 702-706 are the same as or similar to the corresponding steps (steps 202-206) of the exemplary process 200, and thus the detailed explanations are omitted here.

The process 700 then proceeds to a flow determining step 708. In step 708, the flow rate of the target blood vessel may be determined based on the varying status of the integrated values calculated by the integrated value calculating step 706 for the corresponding ROI in the plurality of angiography images and the predetermined correlation between the integrated value and the volume of the contrast agent. Similarly, the predetermined correlation between the integrated value and the volume of the contrast agent may be determined in advance as described above. Therefore, the embodiment makes use of the predetermined correlation between the integrated value and the volume of the contrast agent to determine the flow rate of the target blood vessel under a condition that no external calibration is needed.

In some embodiments, step 708 may include calculating a volume of the contrast agent and determining an average flow rate. In some embodiments, the volumes of the contrast agent in the ROI in the plurality of angiography images may be calculated based on the integrated values of the angiography images and the predetermined correlation. A varying rate of the volume of the contrast agent with respect to time may be calculated for an ascending section of a temporal profile of the volumes of the contrast agent in the ROIs of the angiography images, as the average flow rate of the target blood vessel.

In some embodiments, step 708 may determine the average flow rate even if the volume of the contrast agent is not calculated first. Particularly, at step 708, a varying rate of the integrated value with respect to time may be calculated for an ascending section of a temporal profile of the integrated values for the ROIs in the angiography images, and the varying rate of the integrated value with respect to time may be converted into a varying rate of the volume of the contrast agent with respect to time based on the predetermined correlation between the integrated value and the volume of the contrast agent, as the average flow rate of the target blood vessel.

In an embodiment, the average flow rate may be determined as follows. The volume of the contrast agent as a function of time may be plotted in the coordinate system, as shown by the solid line in FIG. 8. As an example, the contrast agent has not flowed into the ROI during the first 10 seconds, and the injection thereof enters a plateau (i.e., the input is substantially equal to the output) at around 45~60 seconds. After that, the contrast agent flows out of the ROI continuously.

Figure 8:
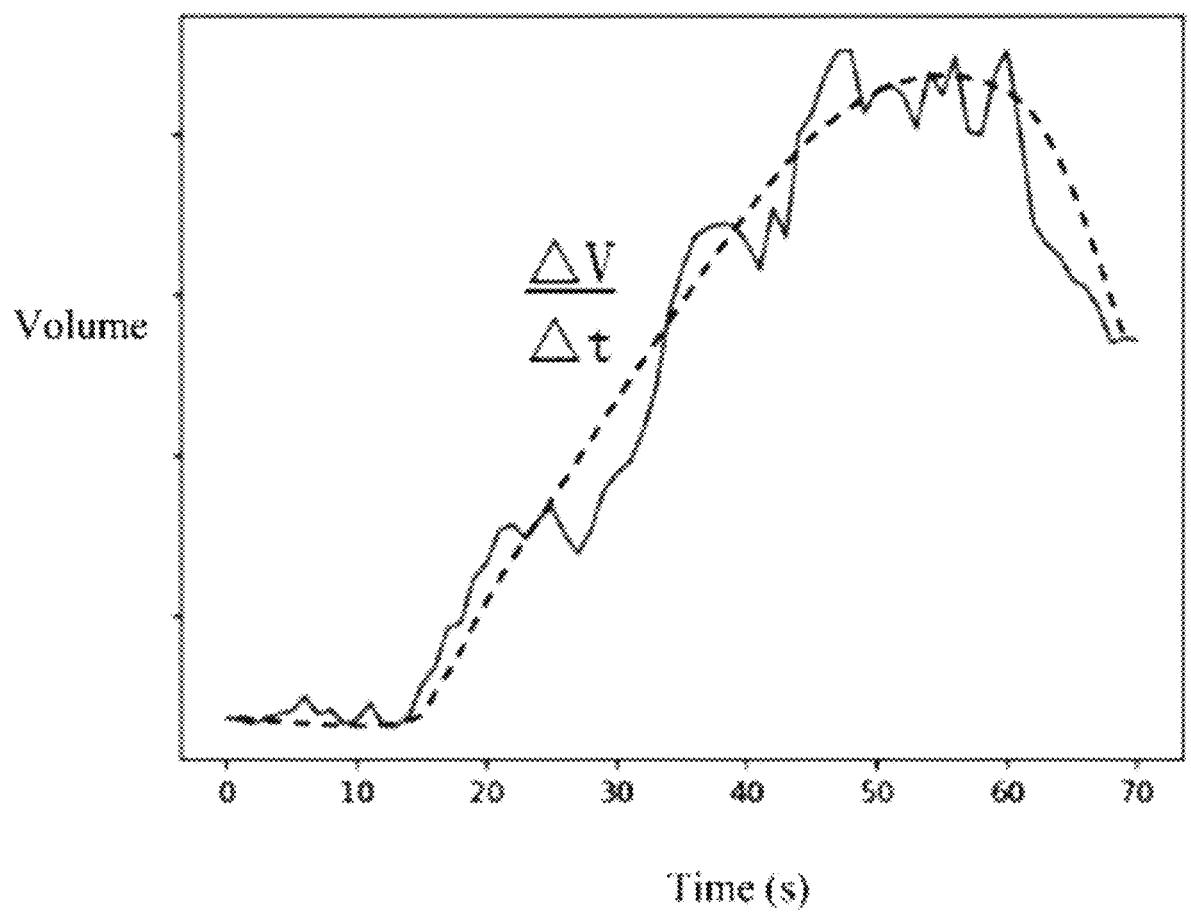
FIG. 8 illustrates a temporal profile of a contrast agent volume varying over time according to an embodiment of the present disclosure.

The temporal profile (as a function of time) may be fitted as a polynomial curve, as shown by the dotted line in FIG. 8. Then, the slope for the ascending section of the polynomial curve may be calculated as the varying rate $$\frac{\Delta V}{\Delta t},$$

which may be determined as the average flow rate of the target blood vessel.

In some embodiments, the plurality of angiography images may be selected from the angiography images acquired after a first predetermined time (which may be set as e.g., about 10 seconds as shown in FIG. 8) elapses from the starting time of the injection and before a second predetermined time (which may be set as e.g., about 40 seconds as shown in FIG. 8) from the starting time of the injection. In this manner, the angiography images acquired within the injection starting time period, plateau time period, and the following period may be excluded. Since the number of the angiography images for flow/lumen volume calculation is decreased, the processing speed may be improved.

Besides, in some embodiments, a part of angiography images may be selected sequentially from the acquired plurality of angiography image sequences to perform the above proceedings for determining lumen volume and/or average flow rate of the blood vessel, to further improve the proceeding speed. In some embodiments, the slope of any section of the described polynomial curve may be calculated as the real-time flow rate of the target blood vessel at the corresponding timing.

Figure 9:
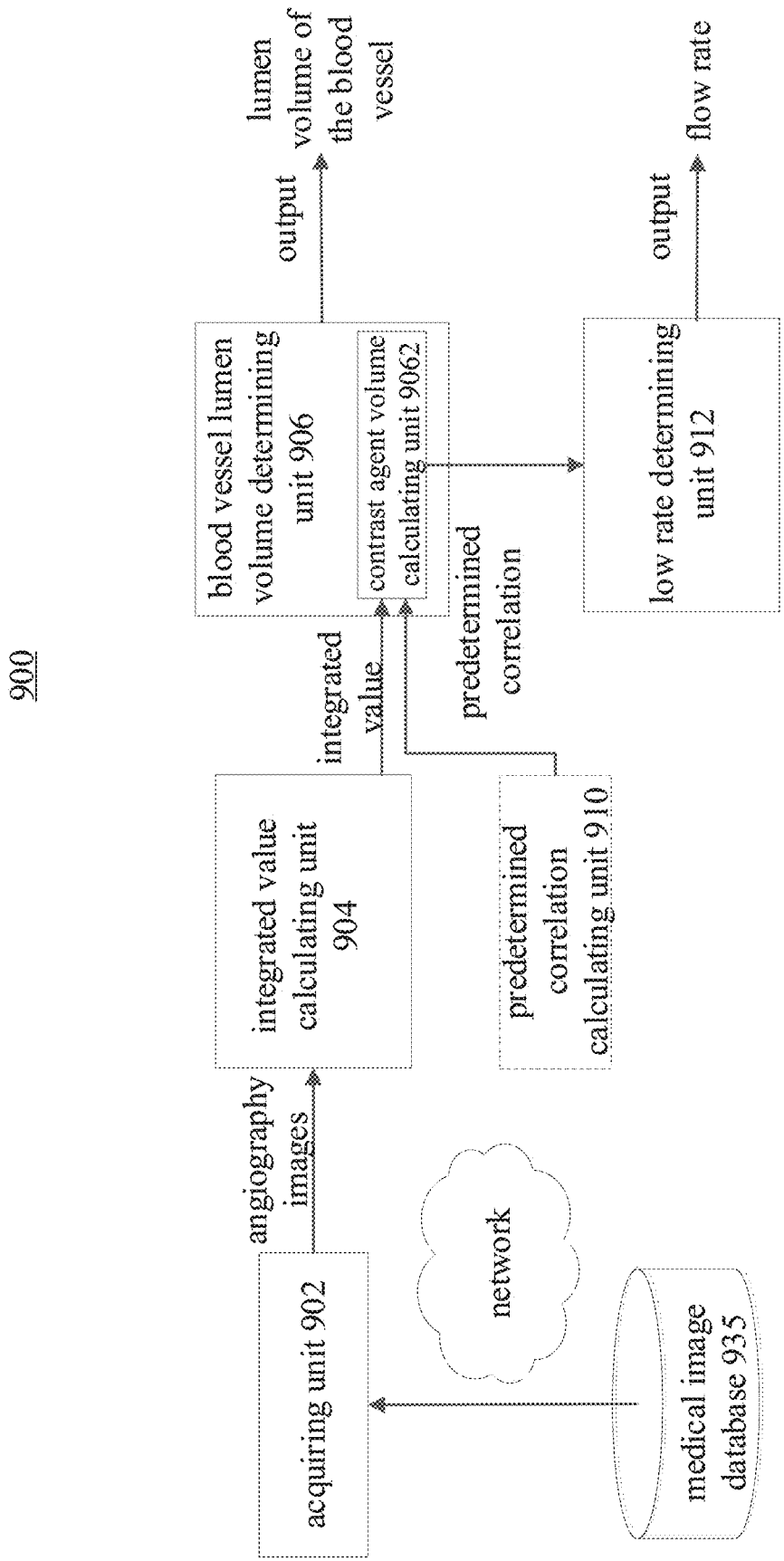
FIG. 9 illustrates a schematic diagram of a device for determining a lumen volume and a coronary blood flow of a target blood vessel according to an embodiment of the present disclosure.

FIG. 9 illustrates a schematic diagram of a device 900 for determining the lumen volume and/or flow of the target blood vessel according to an embodiment of the present disclosure.

The device 900 may include an acquiring unit 902, configured to acquire a temporal sequence of angiography images of the target blood vessel; an integrated value calculating unit 904, configured to identify a corresponding ROI containing the target blood vessel, in each angiography image in a sequence of angiography images, and integrate the background removed and logarithmically processed values of the pixels for the ROI; and a blood vessel lumen volume determining unit 906, configured to determine the lumen volume of the target blood vessel based on the integrated values calculated by the integrated value calculating unit 904 for the plurality of angiography images and the predetermined correlation between the integrated value and the volume of the contrast agent.

In some embodiments, the blood vessel lumen volume determining unit 906 may include a contrast agent volume calculating unit 9062, which may be configured to calculate the volume of the contrast agent within the corresponding ROIs in the plurality of angiography images.

In some embodiments, the acquiring unit 902 may acquire a sequence of angiography images of the target blood vessel from the medical image database 935. In some other embodiments, the acquiring unit 902 may acquire a sequence of angiography images of the target blood vessel from an external device such as a medical image acquisition device (not illustrated). In some embodiments, the acquiring unit 902 may acquire the described images from an image data storage device (not illustrated). In a varied embodiment, the acquiring unit 902 may acquire the needed model and images from at least two of the above image sources. The acquiring unit 902 may transmit the acquired sequence of angiography images of the target blood vessel injected with the contrast agent to the integrated value calculating unit 904.

The integrated value calculating unit 904 may transmit the calculated integrated values to the blood vessel lumen volume determining unit 906, which is configured to determine the lumen volume of the target blood vessel based on the integrated values and the predetermined correlation between the integrated value and the volume of the contrast agent. The predetermined correlation between the integrated value and the volume of the contrast agent may be recalled (retrieved) from e.g. the storage device, and may also be calculated in real-time by a predetermine correlation calculating unit 910.

As an example, the predetermine correlation calculating unit 910 may set sample points for the target blood vessel (e.g. along the centerline of the target blood vessel, but not limited to this) with respect to a certain angiography image by means of the above described methods. As shown in FIG. 5, the values of the integrated signals at the sample points may be plotted against the contrast agent sample volume, and may be fitted as a straight line. The slope of the fitted straight line may be derived to determine the predetermined correlation between the integrated signal and the volume of the contrast agent. Besides, based on Equation (4) and Equation (6), the predetermined correlation may also be determined by the ratio of the integrated signal at a single sample point with respect to the corresponding contrast agent sample volume. However, the predetermined correlation may be acquired with a higher accuracy by means of a plurality of sample points.

In some embodiments, the blood vessel lumen volume determining unit 906 may output the determined lumen volume of the target blood vessel.

In some embodiments, the device 900 may further include a flow rate determining unit 912. The contrast agent volume calculating unit 9062 may transmit the calculated contrast agent volume corresponding to the ROI in each of the plurality of angiography images to the flow rate determining unit 912, so that the flow rate determining unit 912 may determine the flow rate of the target blood vessel based on the varying status of the contrast agent volume in the corresponding ROIs in the plurality of angiography images calculated by the contrast agent volume calculating unit 9062.

In some embodiments, the device 900 may be configured to implement either one of the functions of determining the lumen volume of the target blood vessel and the function of determining the flow rate of the target blood vessel. The units of device 900 may perform the corresponding steps and methods described in this disclosure, and the descriptions are not repeated here.

Figure 10:
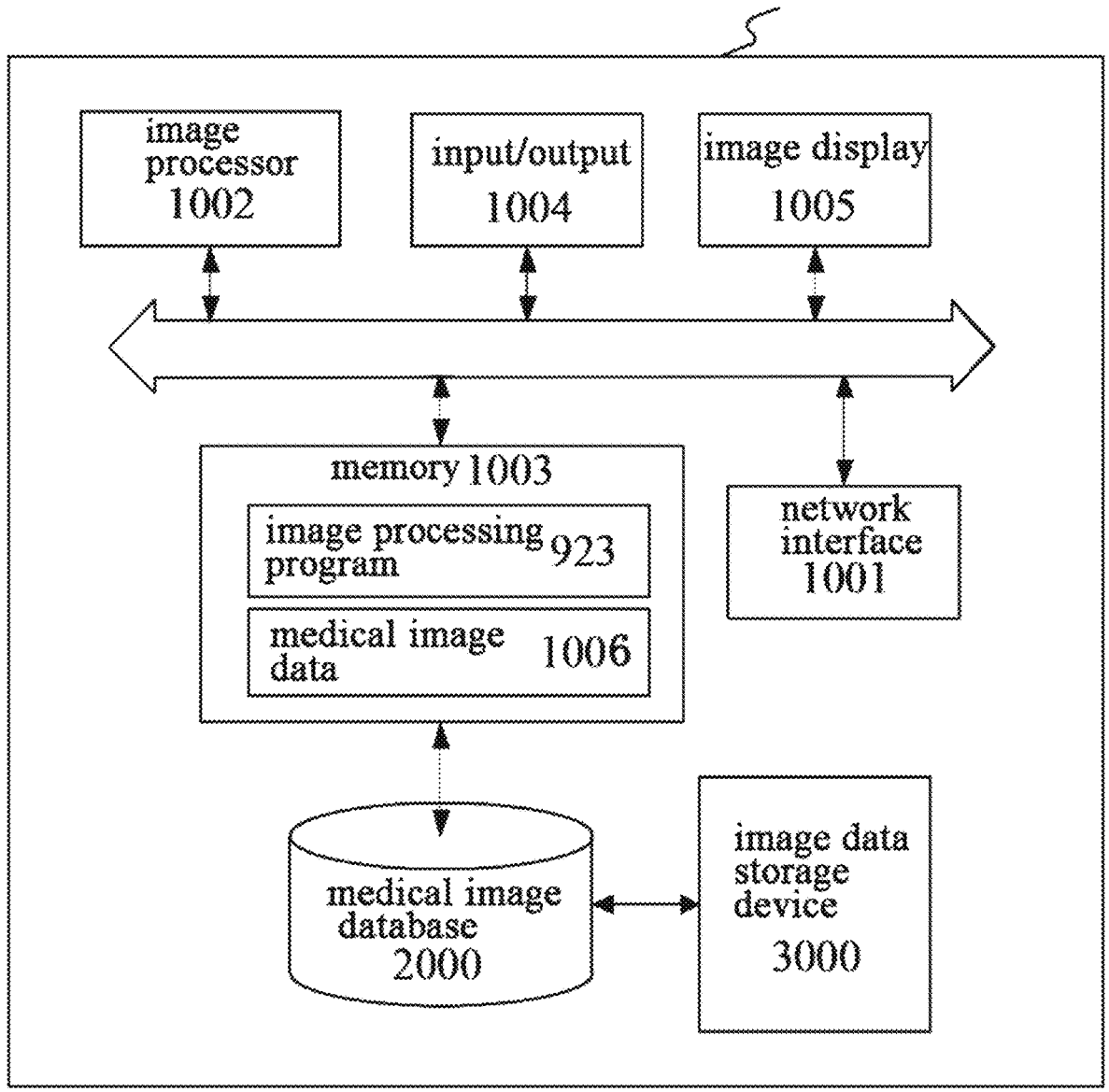
FIG. 10 illustrates a block diagram of a system for determining a lumen volume and a coronary blood flow of a target blood vessel according to an embodiment of present disclosure.

FIG. 10 illustrates a block diagram of a medical image processing system 1000 for determining a lumen volume and an average flow rate of a target blood vessel. The medical image processing system 1000 may include a network interface 1001 by which the system 1000 may be connected to a network (not shown) such as, but not limited to, a local area network in a hospital or the Internet. The network may connect the system 1000 with an external device such as an image acquisition device (not shown), a medical image database 2000, and an image data storage device 3000.

It is contemplated that the devices and methods disclosed in the embodiments may be implemented using a computer device. In some embodiments, the medical image processing system 1000 may be a dedicated smart device or a general-purpose smart device. For example, the medical image processing system 1000 may be a computer customized for image data acquisition and image data processing tasks, or a server placed in the cloud. For example, the system 1000 may be integrated into an image acquisition device.

The medical image processing system 1000 may include an image processor 1002 and a memory 1003, and may additionally include at least one of an input/output 1004 and an image display 1005.

The image processor 1002 may be a processing device including one or more general-purpose processing devices such as a microprocessor, a central processing unit (CPU), a graphics processing unit (GPU), and the like. More specifically, the image processor 1002 may be a complex instruction set computing (CISC) microprocessor, a reduced instruction set computing (RISC) microprocessor, a very long instruction word (VLIW) microprocessor, a processor running other instruction sets, or a processor that runs a combination of instruction sets. The image processor 1002 may also be one or more dedicated processing devices such as application specific integrated circuits (ASICs), field programmable gate arrays (FPGAs), digital signal processors (DSPs), system-on-chip (SoCs), and the like. As would be appreciated by those skilled in the art, in some embodiments, the image processor 1002 may be a special-purpose processor, rather than a general-purpose processor. The image processor 1002 may include one or more known processing devices, such as a microprocessor from the Pentium™, Core™, Xeon™, or Itanium® family manufactured by Intel Corporation, the Turion™, Athlon™, Sempron™, Opteron™, FX™, Phenom™ family manufactured by AMD Corporation, or any of various processors manufactured by Sun Microsystems. The image processor 1002 may also include graphical processing units such as a GPU from the GeForce®, Quadro®, Tesla® family manufactured by Nvidia Corporation, GMA, Iris™ family manufactured by Intel Corporation, or a GPU from the Radeon™ family manufactured by AMD Corporation. The image processor 1002 may also include accelerated processing units such as the Desktop A-4 (6, 8) Series manufactured by AMD Corporation, the Xeon Phi™ family manufactured by Intel Corporation. The disclosed embodiments are not limited to any type of processor(s) or processor circuits otherwise configured to meet the computing demands of identifying, analyzing, maintaining, generating, and/or providing large amounts of imaging data or manipulating such imaging data to determine the lumen volume and flow rate of the target blood vessel, or to manipulate any other type of data consistent with the disclosed embodiments. In addition, the term "processor" or "image processor" may include more than one processor, for example, a multi-core design or a plurality of processors each having a multi-core design. The image processor 1002 can execute sequences of computer program instructions, stored in memory 1003, to perform various operations, processes, methods disclosed herein.

The image processor 1002 may be communicatively coupled to the memory 1003 and configured to execute computer-executable instructions stored therein. The memory 1003 may include a read only memory (ROM), a flash memory, random access memory (RAM), a static memory, volatile or nonvolatile, magnetic, semiconductor, cassette, optical, movable, unmovable, or other types of storage devices or tangible (e.g. non-temporary) computer readable medium. In some embodiments, the memory 1003 may store computer-executable instructions of image processing program(s) 923 and the data generated when the image processing program(s) are performed. The computer program instructions can be accessed by the image processor 1002, read from the ROM, or any other suitable memory location, and loaded in the RAM for execution by the image processor 1002, to implement each step of above methods. The image processor 1002 may also send/receive medical image data to/from the memory 1003. For example, the memory 1003 may store one or more software applications. Software applications stored in the memory 1003 may include, for example, an operating system (not shown) for common computer systems as well as soft-controlled devices. Further, the memory 1003 may store an entire software application or only a part of a software application (e.g. the image processing program (s) 923) to be executable by the image processor 1002. In some embodiments, the image processing program 923 may include the integrated value calculating unit 904 and the blood vessel lumen volume determining unit 906 shown in FIG. 9 as software units, for implementing each step of the method or process for determining the lumen volume of the target blood vessel consistent with the present disclosure. In some embodiments, the image processing program 923 may be executed by the contrast agent volume calculating unit 9062 and the flow rate determining unit 912 shown in FIG. 9, for implementing each step of the method or process for determining the average flow rate of the target blood vessel. In addition, the memory 1003 may store data generated/cached when the computer program is executed, such as medical image data 1006, which includes medical images transmitted from an image acquisition device, the medical image database 2000, the image data storage device 3000, and the like. Besides, the medical image data 1006 may also include detection results of the target blood vessel (blood vessel lumen volume and/or average flow rate).

The image processor 1002 may execute an image processing program 923 to implement a method for determining the lumen volume and/or the average flow rate of the target blood vessel. In some embodiments, when the image processing program 923 is executed, the image processor 1002 may associate the acquired angiography image sequences with the determined lumen volume and/or flow rate of the target blood vessel and store them in the memory 1003. Alternatively, the image processor 1002 may associate the acquired angiography image sequences with the determined lumen volume and/or flow rate of the target blood vessel and send them to the medical image database 2000 via the network interface 1001.

It is contemplated that the device may include one or more processors and one or more memory devices. The processor(s) and storage device(s) may be configured in a centralized or distributed manner. The system 1000 may include one or more digital and/or analog communication device (input/output 1004). For example, the input/output 1004 may include a keyboard and a mouse that allow the user to provide an input.

The system 1000 may be connected to the network through network interface 1001. The network interface 1001 may include a network adapter, a cable connector, a serial connector, a USB connector, a parallel connector, a high-speed data transmission adapter such as optical fiber, USB 3.0, lightning, a wireless network adapter such as a WiFi adapter, a telecommunication (3G, 4G/LTE, etc.) adapters. The network may provide the functionality of local area network (LAN), a wireless network, a cloud computing environment (e.g., software as a service, platform as a service, infrastructure as a service, etc.), a client-server, a wide area network (WAN), and the like.

The system 1000 may further include an image display 1005. In some embodiments, the image display 1005 may be any display device suitable for displaying vascular angiographic image(s) and the detection results thereof. For example, the image display 1005 may be an LCD, CRT, or LED display.

Various operations or functions are described herein that may be implemented as software code or instructions or defined as software code or instructions. Such content may be directly executable source code or difference code ("incremental" or "block" code) ("object" or "executable" form). The software codes or instructions may be stored in a computer-readable storage medium and, when executed, may cause the machine to perform the described functions or operations and include any mechanism for storing information in a form accessible by the machine (e.g., computing devices, electronic systems, etc.), such as recordable or non-recordable media (e.g., read-only memory (ROM), random access memory (RAM), disk storage media, optical storage media, flash memory devices, etc.).

The disclosed device and method of the embodiments may be applied to various imaging modalities where the pixel intensity varies with the distance traveled by imaging particles, such as CT, cone beam computed tomography (CBCT), Spiral CT, positron emission tomography (PET), single-photon emission computed tomography (SPECT), x-ray scan, optical tomography, and radiotherapy portal imaging, etc.

The above embodiments are merely exemplary embodiments of the present invention and are not intended to limit the present invention. The protection scope of the present invention is defined by the claims. Those skilled in the art can make various modifications or equivalent substitutions to the present invention within the spirit and scope of the present invention, and such modifications or equivalents should also be regarded as falling into the protection scope of the present invention.

What is claimed is:

1. A computer-implemented method for determining a lumen volume of a target blood vessel, wherein the computer-implemented method comprises:
    acquiring a temporal sequence of angiography images of the target blood vessel after a contrast agent is injected in the target blood vessel;
    identifying a region of interest containing the target blood vessel, by a processor, in each angiography image in the temporal sequence of angiography images;
    integrating, by the processor, pixel values in each region of interest; and
    determining the lumen volume, by the processor, based on the integrated values of the regions of interest and a predetermined correlation between the integrated values and volumes of the contrast agent, wherein the predetermined correlation is determined based on image analysis of one or more previous temporal sequences of angiography images acquired under the same contrast agent injection condition, wherein the image analysis estimates an angle between a sample vessel captured by each previous temporal sequence of angiography images and an imaging direction, and determines an actual optical path of the sample vessel based on the angle.

2. The method according to claim 1, further comprising determining a flow rate of the target blood vessel, by the processor, based on a varying status of the integrated values and the predetermined correlation between the integrated values and the volumes of the contrast agent.

3. The method according to claim 2, wherein determining the flow rate of the target blood vessel further comprises:
    calculating the volumes of the contrast agent in the regions of interest based on the integrated values calculated for the respective regions of interest and the predetermined correlation; and
    calculating a varying rate of the volumes of the contrast agent with respect to time for an ascending section of a temporal profile of the volumes of the contrast agent in the regions of interests, as the flow rate of the target blood vessel.

4. The method according to claim 2, wherein determining the flow rate of the target blood vessel further comprises:
    calculating, by the processor, a varying rate of the integrated values with respect to time, for an ascending section of a temporal profile of the integrated values for the regions of interests; and
    converting the varying rate of the integrated values with respect to time into a varying rate of the volume of the contrast agent with respect to time based on the predetermined correlation between the integrated values and the volume of the contrast agent, as the flow rate of the target blood vessel.

5. The method according to claim 4, wherein determining the flow rate of the target blood vessel further comprises:
    fitting the temporal profile of the integrated values as a polynomial curve;
    calculating a slope for the ascending section of the polynomial curve as the corresponding varying rate.

6. The method according to claim 1, wherein determining the lumen volume comprises:
    calculating the volumes of the contrast agent in the regions of interest based on the integrated values calculated for the respective regions of interest and the predetermined correlation, and determining the largest one among the calculated volumes of the contrast agent as the lumen volume of the target blood vessel; or
    selecting the largest integrated value in the integrated values calculated for the respective regions of interest, and calculating the volume of the contrast agent corresponding to the largest integrated value as the lumen volume of the target blood vessel based on the largest integrated value and the predetermined correlation.

7. The method according to claim 1, wherein the temporal sequence of angiography images is acquired after a first predetermined time after the injection of the contrast agent starts.

8. The method according to claim 1, wherein the region of interest containing the target blood vessel is obtained along the centerline of the target blood vessel of each angiography image.

9. The method according to claim 1, wherein the regions of interest containing the target blood vessel are tracked across the angiography images using an optical flow algorithm.

10. The method according to claim 1, wherein the predetermined correlation is a linear correlation.

11. The method according to claim 1, wherein the predetermined correlation is determined in advance based on angiography images acquired from a previous angiography of a same patient under the same contrast agent injection condition, or based on angiography images acquired from part of the target blood vessel under the same contrast agent injection condition.

12. The method according to claim 1, wherein integrating the pixel values further comprises:
    calculating a first processed image by removing a background from and performing logarithmical processing on each region of interest; and
    summing the intensity values of the pixels in the first processed image.

13. The method according to claim 12, when calculating the first processed image further comprises:
    calculating a second processed image by determining a logarithm of each pixel value;
    inpainting the target blood vessel in the angiography image based on intensity values of background pixels of its periphery;
    calculating a third processed image by determining a logarithm of each pixel value of the inpainted angiography image; and subtracting the third processed image from the second processed image to obtain the first processed image.

14. The method according to claim 1, wherein the target blood vessel is a diseased blood vessel.

15. The method according to claim 1, wherein the image analysis further estimates a diameter of the sample vessel captured by each previous temporal sequence of angiography images and determines the actual optical path of the sample vessel based on both the diameter and the angle.

16. A system for determining a lumen volume of a target blood vessel, comprising:
an interface configured to receive a temporal sequence of angiography images of the target blood vessel acquired after a contrast agent is injected in the target blood vessel; and
a processor configured to:
identify a region of interest containing the target blood vessel in each angiography image in the temporal sequence of angiography images;
integrate pixel values in each region of interest; and
determine the lumen volume based on the integrated values of the regions of interest and a predetermined correlation between the integrated values and volumes of the contrast agent, wherein the predetermined correlation is determined based on image analysis of one or more previous temporal sequences of angiography images acquired under the same contrast agent injection condition, wherein the image analysis estimates an angle between a sample vessel captured by each previous temporal sequence of angiography images and an imaging direction, and determines an actual optical path of the sample vessel based on the angle.

17. The system according to claim 16, wherein the processor is further configured to determine a flow rate of the target blood vessel based on a varying status of the integrated values and the predetermined correlation between the integrated values and the volumes of the contrast agent.

18. The system according to claim 16, wherein the temporal sequence of angiography images is acquired after a first predetermined time after the injection of the contrast agent starts.

19. The system according to claim 16, wherein the region of interest containing the target blood vessel is obtained along the centerline of the target blood vessel of each angiography image.

20. The system according to claim 16, wherein the processor is further configured to:
calculate a processed image by removing a background from and performing logarithmical processing on each region of interest; and
sum the intensity values of the pixels in the processed image.

21. A non-transitory computer-readable storage medium having computer executable codes stored thereon, the computer executable codes, when executed by a processor, performing a method for determining a lumen volume of a target blood vessel, wherein method comprises:
receiving a temporal sequence of angiography images of the target blood vessel acquired after a contrast agent is injected in the target blood vessel;
identifying a region of interest containing the target blood vessel in each angiography age in the temporal sequence of angiography images;
integrating pixel values in each region of interest; and
determining the lumen volume based on the integrated values of the regions of interest and a predetermined correlation between the integrated values and volumes of the contrast agent, wherein the predetermined correlation is determined based on image analysis of one or more previous temporal sequences of angiography images acquired under the same contrast agent injection condition, wherein the image analysis estimates an angle between a sample vessel captured by each previous temporal sequence of angiography images and an imaging direction, and determines an actual optical path of the sample vessel based on the angle.

* * * * *